United States Patent
Marrosu et al.

(10) Patent No.: US 7,996,088 B2
(45) Date of Patent: Aug. 9, 2011

(54) VAGUS NERVE STIMULATION BY ELECTRICAL SIGNALS FOR CONTROLLING CEREBELLAR TREMOR

(75) Inventors: Francesco Marrosu, Capoterra, CA (US); Maria Giovanna Marrosu, Capoterra, CA (US)

(73) Assignee: Cyberonics, Inc., Houston, TX (US)

( * ) Notice: Subject to any disclaimer, the term of this patent is extended or adjusted under 35 U.S.C. 154(b) by 1173 days.

(21) Appl. No.: 11/460,155

(22) Filed: Jul. 26, 2006

(65) Prior Publication Data

US 2008/0027503 A1 Jan. 31, 2008

(51) Int. Cl.
*A61N 1/32* (2006.01)
(52) U.S. Cl. .......................................... 607/45
(58) Field of Classification Search .................. 607/45, 607/48–50, 62, 118; 600/544–548
See application file for complete search history.

(56) References Cited

U.S. PATENT DOCUMENTS

| | | | | |
|---|---|---|---|---|
| 4,702,254 A * | 10/1987 | Zabara | ............................ | 607/45 |
| 4,867,164 A * | 9/1989 | Zabara | ............................ | 607/45 |
| 5,700,282 A | 12/1997 | Zabara | | |
| 6,356,784 B1 * | 3/2002 | Lozano et al. | ..................... | 607/2 |
| 7,167,751 B1 * | 1/2007 | Whitehurst et al. | ............ | 607/40 |
| 2002/0099418 A1 * | 7/2002 | Naritoku et al. | ................ | 607/45 |
| 2004/0193220 A1 * | 9/2004 | Whitehurst et al. | ............. | 607/3 |
| 2004/0243182 A1 | 12/2004 | Cohen et al. | | |
| 2005/0021103 A1 * | 1/2005 | DiLorenzo | ...................... | 607/45 |
| 2005/0070970 A1 * | 3/2005 | Knudson et al. | ................ | 607/45 |

OTHER PUBLICATIONS

Vagus nerve stimulation for essential tremor: A pilot efficacy and safety trial; A. Handforth, W. G. Ondo, S. Tatter, G. W. Mathern, R. K. Simpson, Jr., F. Walker, J. P. Sutton, J. P. Hubble, and J. Jankovic; Neurology 2003; 61; 1401-1405.

Vagal nerve stimulation effects on cerebellar tremor in multiple sclerosis; F. Marrosu, MD; A. Maleci, MD; E. Cocco, MD; M. Puligheddu, MD; and M.G. Marrosu, MD; Neurology 2005; 65; 490.

* cited by examiner

*Primary Examiner* — Carl H Layno
*Assistant Examiner* — Jessica Sarcione
(74) *Attorney, Agent, or Firm* — Williams, Morgan & Amerson, P.C.; Jonathan D. Riwell; Darrell N. Fuller

(57) ABSTRACT

A neurostimulator system for alleviating cerebellar tremor associated with multiple sclerosis, for instance, comprises a programmable electrical pulse generator. The programmable electrical pulse generator is programmed to generate electrical signals with the following parameters: a current magnitude of about 1 mA or less, a stimulation signal on-time to signal off-time ratio in the range of 2:1 to 1:1.8, signal on-times and off-times in the range of about 10 seconds to about 5 minutes, a signal frequency below 15 Hz, and a pulse width within the range of 50 μs to 300 μs. Other embodiments are disclosed and claimed.

24 Claims, 5 Drawing Sheets

VAGUS NERVE STIMULATION BY ELECTRICAL SIGNALS FOR CONTROLLING CEREBELLAR TREMOR

BACKGROUND OF THE INVENTION

1. Field of the Invention

The present invention relates to stimulation of a cranial nerve by electrical pulsed signals and, in particular, to the manufacture of a system for electrical stimulation of the vagus nerve and the use of an electrical pulse generator for such a system applicable to the vagus nerve for improving control of cerebellar tremor, particularly, cerebellar tremor associated with multiple sclerosis.

2. Description of Related Art

Patients suffering from multiple sclerosis (MS) show a broad variety of symptoms. Patients diagnosed with MS, e.g., according to the Poser criteria, typically show postural and intentional non-persistent or persistent cerebellar tremor (CT).

Conventionally, patients suffering from MS are treated pharmacologically with drugs or biologically active compounds such as antibiotics or polypeptides. Exemplary pharmaceutical treatments include Interferon β-1b and β-1a. Moreover, several cycles of immunoglobulins may also be administered. Anticonvulsants, e.g., primidone, may alleviate CT by controlling nerve impulses in the brain. In the case of acute relapses corticosteroids are applied.

However, pharmacological treatment may not only result in undesirable side effects but also often proves not sufficiently successful.

Direct electrical stimulation of cranial nerves affecting a variety of brain areas has been successfully used to treat patients for a variety of diseases including epilepsy/epileptic seizures, eating disorders, and depression. Neurocybernetic prostheses as described in the U.S. Pat. No. 4,702,254, has been proven successful in the controlling of epileptic seizures by applying pulsed electrical signals to the vagus nerve.

However, the vagus nerve comprises some 100,000 fibers (axons) of different sizes, generally classified as A, B and C fibers, where A and B fibers are myelinated in contrast to C fibers. Among these fibers are axons conducting signals to the brain (visceral afferents) and nerve fibers conducting signal in the opposite direction (efferents). A, B, and C fibers differ, e.g., in electrical stimulation thresholds and electrical conduction velocities. Individual nerve fibers (whether A, B, or C fibers) generally conduct signals in only one direction. Electrical stimulation of a cranial nerve trunk such as the left or right vagus nerve branches typically generates action potentials both to and from the brain among different (A, B and C) types of nerve fibers. It has been suggested that generally the effects of vagus nerve stimulation are mediated via the nucleus tractus solitarius, the main site of visceral afferent complex termination in the brain, projecting bilaterally to the cerebellum.

Despite the recognition that cranial nerve stimulation may be an appropriate treatment for several movement disorders, e.g., epileptic seizures, the fact that detailed neural pathways for many (if not all) cranial nerves remain unknown makes predictions of efficacy for any given condition or disorder impossible. Moreover, even if such pathways were known, the precise stimulation parameters that would energize particular pathways that affect a particular disorder of interest cannot readily be predicted.

Consequently, electrical stimulation discriminating of a specific kind of nerve fibers, and for particular neural pathways, i.e. neurocybernetic spectral discrimination, represents a tremendous challenge.

BRIEF SUMMARY OF THE INVENTION

Notwithstanding the complexity of neurostimulation for the treatment of particular conditions, it is an object of the present invention to provide methods and devices for alleviating cerebellar tremor (ataxia) associated with MS.

In accordance with certain embodiments of the present invention, a neurostimulator system for alleviating cerebellar tremor, as may be associated with multiple sclerosis, is provided. The system comprises a programmable electrical pulse generator; and at least one electrode connected to the programmable electrical pulse generator; and wherein the programmable electrical pulse generator is programmed to generate electrical signals with the following parameters: a signal frequency of 30 Hz or less, preferably 15 Hz or less, a current magnitude of not above 3 mA, preferably not above 1 mA, a stimulation signal on-time to signal off-time ratio in the range of from about 10:1 to about 1:10, more preferably from about 2:1 to about 1:2, and signal on-times and off-times in the range of about 10 seconds to about 5 minutes, and a pulse width within the range of 50 µs to 1000 µs, more preferably within the range of about 50 µs to 500 µs.

In some embodiments, the neurostimulator system further comprises an electroencephalographic sensor means configured to detect the presence, the onset or precursors of cerebellar tremor associated with multiple sclerosis by sensing the electroencephalographic waves and to output at least one first sensor signal to the electrical pulse generator, and wherein the electrical pulse generator is configured to generate electrical signals on the basis of the at least one sensor signal.

In some embodiments, an above-described neurostimulator system further comprises a tremor sensor connected with the programmable electrical pulse generator and configured to sense tremor associated with multiple sclerosis and to generate at least one second sensor signal and to transmit the sensor signal to the programmable electrical pulse generator and wherein the electrical pulse generator is configured to generate electrical signals on the basis of the at least one sensor signal.

In some embodiments, an above-described neurostimulator system further comprises a muscular sensor connected with the programmable electrical pulse generator and configured to sense muscle activity (e.g., spontaneous muscle activity), and to generate at least one third sensor signal and to transmit the sensor signal to the programmable electrical pulse generator and wherein the electrical pulse generator is configured to generate electrical signals on the basis of the at least one sensor signal.

In certain embodiments, an above-described neurostimulator system comprises a first electrode and a second electrode wherein the first electrode has a negative potential with respect to the second electrode.

Also provided in accordance with certain embodiments of the present invention is a method for manufacturing a neurostimulator system intended for alleviating cerebellar tremor associated with multiple sclerosis. The manufacturing method comprises providing a programmable electrical pulse generator; programming the programmable electrical pulse generator to generate electrical signals effective to control cerebellar tremor when said signals are applied to a cranial nerve of a patient suffering from cerebellar tremor; and providing at least one electrode connected with the programmable electrical pulse generator for applying the electrical signals generated by the electrical pulse generator to a cranial nerve for controlling cerebellar tremor.

In certain embodiments of this method, the electrical signals are pulsed waveform signals. In certain embodiments, the method includes programming the pulse generator includes providing for the electrical signals to be delivered continuously or periodically or intermittently and/or on the patient's demand. In some embodiments, the programmable electrical pulse generator is programmed by programmable parameters comprising a pulse width and/or a current magnitude and/or a pulse frequency and/or stimulation on-time and/or stimulation off-time. In some embodiments, the following programmable parameters are chosen: a current magnitude of not above 3 mA, more preferably, not above 1 mA, a stimulation signal on-time to signal off-time ratio in the range of from about 10:1 to about 1:10, more preferably from about 2:1 to about 1:2, and signal on-times and off-times in the range of about 10 seconds to about 5 minutes, a signal frequency below a frequency of 30 Hz, preferably 15 Hz or less, and a pulse width within the interval of 50 μs to 1000 μs, more preferably within the range of about 50 μs to 500 μs.

In certain embodiments of an above-described method, the neurostimulator system comprises a first electrode and a second electrode and wherein the first electrode has a negative potential with respect to the second electrode.

In certain embodiments the manufacturing method further comprises providing a sensor means configured to sensor the presence, onset or precursors of cerebellar tremor, as associated with multiple sclerosis, for example, by sensing the electroencephalographic waves and to output at least one sensor signal to the electrical pulse generator, and wherein the electrical pulse generator is configured to generate electrical signals on the basis of the at least one sensor signal.

Certain embodiments of the manufacturing method further comprise providing a muscular sensor configured to sense the presence, onset or precursors of cerebellar tremor by sensing the spontaneous muscle activity and to output at least one muscle sensor signal to the electrical pulse generator, wherein the electrical pulse generator is configured to generate electrical signals on the basis of the at least one muscle sensor signal.

In accordance with still another embodiment of the present invention a method of treating a patient suffering from cerebellar tremor is provided which comprises: obtaining a neurostimulator system comprising a programmable electrical pulse generator comprising at least one electrode for applying electrical signals generated by the electrical pulse generator, wherein said pulse generator is programmed with signal parameters comprising a pulse width and/or a current magnitude and/or a pulse frequency and/or stimulation on-time and/or stimulation off-time effective to attenuate or control cerebellar tremor in the patient. The method of treatment further comprises placing said electrode in electrical communication with a cranial nerve of the patient; and applying said electrical signals to said cranial nerve by means of the at least one electrode, effective to attenuate or control the cerebellar tremor.

In some embodiments, the cerebellar tremor is associated with multiple sclerosis. In some embodiments, the electrical signals are pulsed waveform signals. In some embodiments, the electrical signals are applied continuously or periodically or intermittently and/or on the patient's demand. In some embodiments, the following programmable parameters are chosen: the current magnitude is set to a value not above 3 mA, preferably not above 1 mA, a stimulation signal on-time to signal off-time ratio in the range of about 10:1 to about 1:10, more preferably from about 2:1 to about 1:2, and signal on-times and off-times in the range of about 10 seconds to about 5 minutes, the signal frequency is set to a value below 30 Hz, more preferably about 15 Hz or less, and the pulse width is set to a value within the interval of 50 μs to 1000 μs, more preferably within the range of about 50 μs and 500 μs.

In some embodiments of an above-described method of treatment, the at least one electrode comprises first and second electrodes and the electrical signals are applied by said first electrode and said second electrode wherein the first electrode has a negative potential with respect to the second electrode and wherein the first electrode is applied proximal to the brain and the second electrode is applied distal to the brain with respect to the first electrode.

In some embodiments, the neurostimulator system employed in the method of treatment comprises a sensor configured to sense the onset or precursors of cerebellar tremor and wherein the electrical pulse generator is configured to generate electrical signals on the basis of at least one sensor signal. The method further comprises sensing the electroencephalographic waves and outputting at least one sensor signal to the electrical pulse generator.

In certain embodiments, an above-described method of treatment employs a neurostimulator system which comprises a muscular sensor configured to sense the onset or precursors of cerebellar tremor (e.g., associated with multiple sclerosis) by sensing the muscle activity (e.g., spontaneous muscle activity), and to output at least one muscular sensor signal to the electrical pulse generator, and wherein the electrical pulse generator is configured to generate electrical signals on the basis of the at least one muscular sensor signal.

In accordance with still another embodiment of the present invention, a computer program product is provided which comprises one or more computer readable media having computer-executable instructions for controlling a programmable electrical pulse generator to generate electrical signals with a current magnitude of not above 2 mA, in particular, not above 1 mA, a stimulation signal on-time to signal off-time ratio in the range of about 2:1 to about 1:2, and signal on-times and off-times in the range of about 10 seconds to about 5 minutes, a signal frequency below 30 Hz, and a pulse width within the interval of 50 μs and 500 μs.

These and other embodiments, features and advantages will be apparent from the following description and drawings.

DETAILED DESCRIPTION OF PREFERRED EMBODIMENTS

Figure 1:
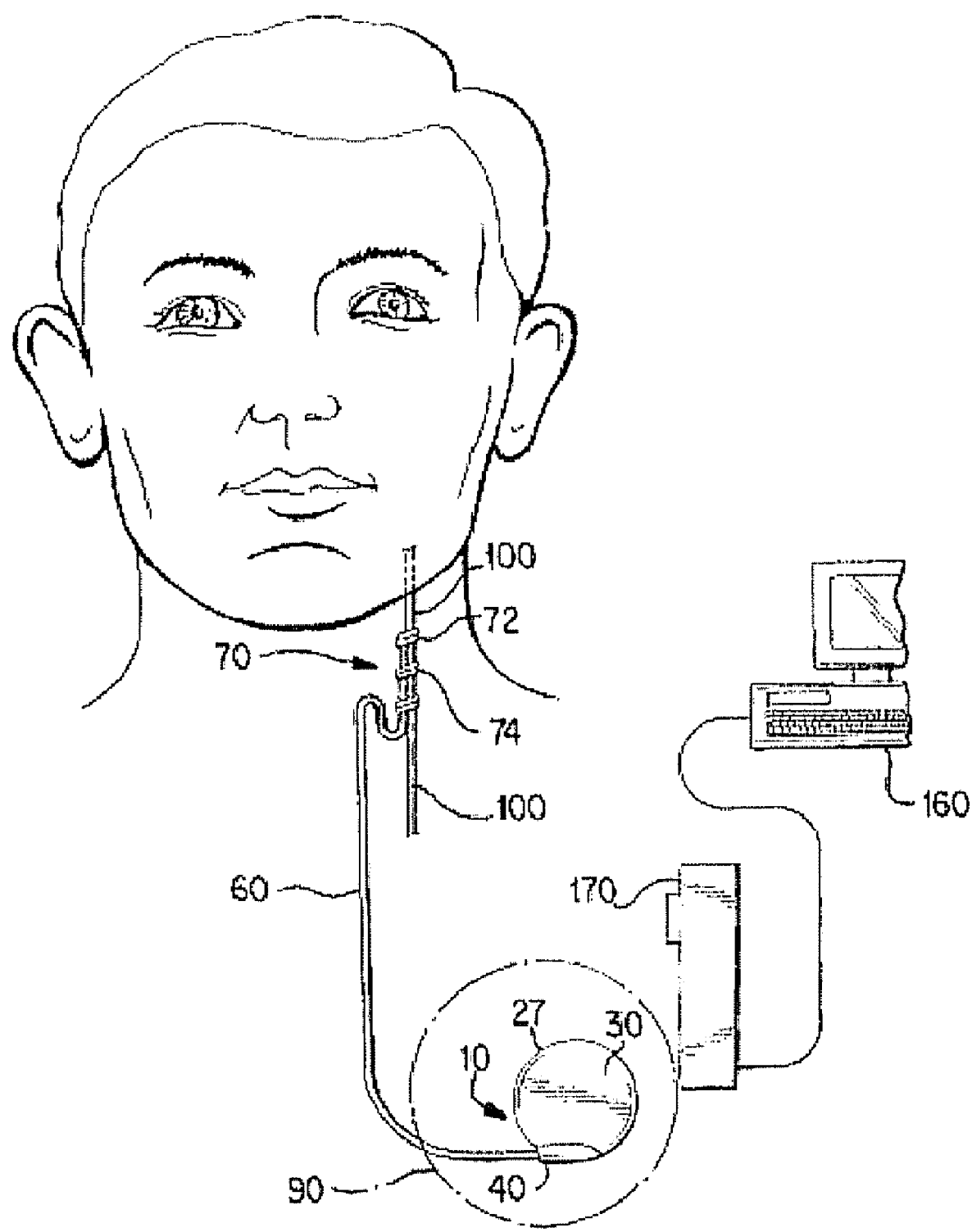
FIG. 1 is a simplified illustration of an implantable pulse generator (neurostimulator device) for stimulus generation with associated lead-electrode system implanted in a patient's body for stimulating a vagus nerve, and showing a related external program console, in accordance with an embodiment of the present invention.

The above-mentioned object is achieved by a system that provides a neurostimulator system for alleviating cerebellar tremor, particularly cerebellar tremor associated with multiple sclerosis, comprising a programmable electrical pulse generator; and at least one electrode connected to the programmable electrical pulse generator; and wherein the programmable electrical pulse generator is programmed to generate electrical signals with the following parameters: a signal frequency of 30 Hz or less, preferably 15 Hz or less, and a current magnitude of 3 mA or less, preferably 1 mA or less, a stimulation signal on-time to stimulation signal off-time ratio within a range of about 10:1 to about 1:10, more preferably from about 2:1 to about 1:2, and preferably about 1:1, and on-times and off-times in the range of about 10 seconds to about 5 minutes, more preferably from about 30 to about 60 seconds, and a pulse width within the range of about 50 µs to 1000 µs, preferably within the range of about 50 µs to 500 µs, more preferably within the range of about 200 µs to 300 µs.

Neurostimulator systems of the present invention may comprise an external electrical pulse generator or an implanted pulse generator, with implantable generators being preferred. The implanted pulse generator may comprise circuitry and a battery enclosed within a shell or case of a biocompatible material such as titanium suitable for implantation, and having one or more connectors for connecting to leads.

The pulse generator is preferably directly coupled to the electrode(s) via one or more leads, although electromagnetic inductive coupling and RF signal coupling may also be employed. In a preferred embodiment, electrode leads may pass from the circuitry of the electrical pulse generator through a channel formed subcutaneously toward, e.g., the neck of a patient where the at least one electrode is coupled to the patient's vagus nerve. Preferably, the at least one electrode comprises a stimulating electrode assembly comprising a bipolar electrode pair coupled to the patient's vagus nerve.

Spiral-shaped electrodes, such as those disclosed in U.S. Pat. No. 4,573,481, may be wrapped about the vagus nerve. Suitable spiral-shaped electrodes are available from Cyberonics, Inc. (Houston, Tex.) as the Model 302 lead. However, the present invention also comprises embodiments in which the at least one electrode does not directly contact the vagus nerve. It is preferred to couple the electrodes to the left vagus nerve, although attachment to the right vagus nerve, or to both the left and right vagus nerves may be employed in alternative embodiments.

The present inventors have surprisingly discovered that the inventive system programmed as described above provides a means for improved control of cerebellar tremor (CT) in multiple sclerosis (MS) patients. The exact mechanism and thus the explanation for the positive result obtained by the inventive system is, however, yet unknown.

An external programming system capable of wireless (i.e., radio frequency) communication with the (preferably implanted) electrical pulse generator may be used to program the generator with a therapeutic electrical signal characterized by programmable parameters such as current amplitude, pulse width, pulse frequency, signal on-time and signal off-time. The external programming system may comprise an RF transmitter and receiver, and a computer, e.g., a handheld computer operable by a healthcare provider. Communications systems operating in the recently established medical implant communication service (MICS) band at 402-405 MHz are suitable, although prior art systems using other communications protocols are more conventionally used.

It has been empirically determined that in the context of control of CT associated with MS, preferred parameter ranges for the programmable parameters are defined by a signal frequency of 30 Hz or less, preferably 15 Hz or less, more preferably about 10 Hz; a current magnitude of 3 mA or less, and preferably 1 mA or less; a stimulation signal on-time to signal off-time ratio in the range of about 2:1 to about 1:2, preferably about 1:1, with signal on-times and off-times in the range from about 10 seconds to about 5 minutes; and a pulse width within the range of about 50 µs to about 500 µs, preferably from about 200 µs to about 300 µs.

The foregoing parameters specify a relatively (with respect to the context of epilepsy) low frequency, high duty-cycle (i.e., high ratio of signal on-time to off-time) stimulation regime. In one embodiment the pulse width is chosen to be between 200 µs and 300 µs, i.e. between the values for relatively narrow pulse widths used to stimulate mainly A and B fibers and pulse widths that are typically required for stimulating C fibers that exhibit relatively high stimulation thresholds.

In contrast to the stimulation parameters appropriate for the present invention, typical vagus nerve stimulation parameters for controlling epileptic seizures typically employ signal frequencies between 20 and 30 Hz, signal on-time to off-time ratios of about 1:10 (about 30 seconds on-time and about 5 minutes off-time), current magnitudes greater than 1.5 mA, and pulse widths of between 300 and 400 µs.

The electrical signals generated by the electrical pulse generator are preferably pulsed electrical signals comprising waveforms that can be readily generated by electrical pulse generators known in the art, and that are preferably sufficient to induce afferent and/or efferent action potentials on the patient's vagus nerve.

According to an embodiment the system may comprise an electroencephalographic sensor means 410 configured to sensor sense the onset or precursors of cerebellar tremor associated with multiple sclerosis by sensing electroencephalographic waves and to output at least one first sensor signal to the electrical pulse generator, and wherein the electrical pulse generator is configured to general electrical signals on the basis of the at least on first sensor signal.

Alternatively or in addition, the system may comprise a tremor sensor 510 as, e.g., a sensor attached to the skin for determining low-frequency (about 4 Hz) trembling, connected with the programmable electrical pulse generator and configured to sense tremor caused by multiple sclerosis and to generate at least one second sensor signal and to transmit the sensor signal to the programmable electrical pulse generator and wherein the electrical pulse generator is configured to generate electrical signals on the basis of the at least one second sensor signal.

Alternatively or in addition, the system may comprise a muscular sensor 610 connected with the programmable electrical pulse generator and configured to sense muscle activity, in particular, spontaneous muscle activity, and to generate at least on third sensor signal and to transmit the sensor signal to the programmable electrical pulse generator and wherein the electrical pulse generator is configured to generate electrical signals on the basis of the at least one third sensor signal.

According to the foregoing alternative embodiments, delivery of a therapeutic electrical signal to a cranial nerve of the patient occurs in response to one or more sensor signals. Such stimulation is frequently referred to as "active" stimulation, as opposed to stimulation solely according to an on/off cycle, which is generally referred to as "passive" stimulation. In certain embodiments, the system may deliver the electrical signal to the vagus nerve of the patient only if one or more sensor signals indicate a precursor state or the onset or the intensification of a CT associated with MS. The tremor sensor may be attached supracutaneously and may detect vibrations of the skin characteristic for low-frequency intention tremor with frequencies up to 4 Hz, for example. In other embodiments, however, the electrical signal may be delivered both by active and by passive stimulation.

Systems of the present invention preferably comprise an electrode pair for delivering a pulsed electrical signal to the cranial nerve to treat the CT. The electrode pair preferably comprises a first electrode and a second electrode wherein the first electrode has a negative potential with respect to the second electrode, in particular, a cathode and an anode, with the cathode located nearer to the brain of the patient than the anode, i.e., the cathode is applied proximal to the brain and the anode will be applied distal to the brain with respect to the cathode.

The above mentioned object is also achieved by providing a method for manufacturing a neurostimulator system for alleviating cerebellar tremor associated with multiple sclerosis, comprising providing a programmable electrical pulse generator; programming the programmable electrical pulse generator to generate electrical signals; providing at least one electrode connected with the programmable electrical pulse generator for applying the electrical signals generated by the electrical pulse generator to a cranial nerve, preferably the vagus nerve, for controlling the cerebellar tremor.

By this method for manufacturing a neurostimulator system one is enabled to obtain means for an improving or eliminating the cerebellar tremor, particularly where the tremor is associated with multiple sclerosis.

The neurostimulator system is preferably manufactured in such a way that the electrical signals are generated as pulsed waveform signals that can readily be applied continuously or periodically or intermittently and/or on the patient's demand with a well-defined intensity, frequency, etc.

Thus, the application of electrical signals may be performed chronically, acutely, or both. In certain embodiments, systems of the invention may comprise an acute therapeutic signal to be administered during a first, acute period of treatment and a chronic therapeutic signal to be administered during a second, chronic treatment period. The patient may be able to activate, by manual means such as a magnet, the acute treatment algorithm to provide immediate intervention for improving control of CT tremor.

According to an embodiment of the method the programmable electrical pulse generator is programmed by setting programmable parameters comprising one or more of a pulse frequency, a current magnitude, a pulse width, stimulation on-time, and stimulation off-time.

Preferably, in the context of cerebellar tremor associated with multiple sclerosis, the programmable parameters are chosen as: a signal frequency of 30 Hz or less, and preferably 15 Hz or less, more preferably about 10 Hz or less; a current magnitude of 3 mA or less, preferably 1 mA or less; a stimulation signal on-time to signal off-time ratio in the range of about 2:1 to about 1:2, preferably about 1:1 and specifically about 60 seconds on-time and 60 seconds off-time; and a pulse width within the range of about 50 µs to about 500 µs, preferably from about 200 µs to about 300 µs.

The inventive method for manufacturing a neurostimulator system may employ an electrode pair comprising a cathode and an anode.

Moreover, the method may comprise providing a sensor means configured to sense the presence, onset or precursors of cerebellar tremor associated with multiple sclerosis, in particular, by sensing the electroencephalographic waves of the patient and sending at least one sensor signal to the electrical pulse generator, to which sensor signal the responds by generating a therapeutic electrical signal defined by programmed parameters.

The method may also providing a muscular sensor configured to sensor the onset or precursors of the onset of cerebellar tremor, in particular, caused by multiple sclerosis, by sensing spontaneous muscle activity and to output at least one muscle sensor signal to the electrical pulse generator, and wherein the electrical pulse generator is configured to generate electrical signals on the basis of the at least one muscle sensor signal.

The above mentioned object is also achieved by providing use of a programmable electrical pulse generator for the manufacture of a neurostimulator system comprising at least one electrode for applying electrical signals generated by the electrical pulse generator by means of the at least one electrode to a cranial nerve, preferably the vagus nerve, for controlling cerebellar tremor.

This kind of use is particularly suitable, if the cerebellar tremor present in a patient having multiple sclerosis. The electrical signals preferably comprise pulsed waveform signals that may be applied continuously, periodically, intermittently and/or on the patient's demand.

The pulse generator used for the manufacture of the neurostimulator system is preferably programmable to define the generated electrical signals in terms of a number of programmable parameters including the current magnitude, the signal frequency, the pulse width of the signals as well as the stimulation on-time (time period of signal generation for stimulating the nerve) and stimulation off-time (time period of no signal generation allowing the nerve to recover from the stimulation). Preferred parameters may be specified as follows: the current magnitude may be programmed to a value not above 3 mA, preferably not above 1 mA; the stimulation signal on-time to signal off-time ratio may be programmed in the range of about 2:1 to about 1:2, preferably about 1:1, with signal on-times and off-times programmed in the range from about 10 seconds to about 5 minutes, preferably about 60 seconds each; the signal frequency may be programmed to a value of 30 Hz or less, preferably 15 Hz or less, and more preferably about 10 Hz; and the pulse width may be programmed to a value within the range of about 50 µs to about 500 µs, preferably from about 200 µs to about 300 µs.

The electrical signals may be applied by a first electrode and a second electrode, wherein the first electrode has a negative potential with respect to the second electrode and wherein the first electrode is applied proximal to the brain and the second electrode is applied distal to the brain with respect to the first electrode.

According to another embodiment of the use of a programmable electrical pulse generator for the manufacture of a neurostimulator system this system may comprise a sensor means configured to sensor the onset or precursors of the onset of cerebellar tremor, in particular, caused by multiple sclerosis, in particular, by sensing the electroencephalographic waves and to output at least one sensor signal to the electrical pulse generator, and wherein the electrical pulse generator is configured to generate electrical signals on the basis of the at least one sensor signal.

In particular, the system may comprise a muscular sensor configured to sensor the onset or precursors of cerebellar tremor associated with multiple sclerosis, by sensing the spontaneous muscle activity, and to output at least one muscle sensor signal to the electrical pulse generator, and wherein the electrical pulse generator is configured to generate electrical signals on the basis of the at least one muscle sensor signal.

Moreover, it is provided a computer program product comprising one or more computer readable media having computer-executable instructions for controlling the programmable electrical pulse generator to generate electrical signals with a current magnitude not above 3 mA, preferably not above 1 mA; a stimulation signal on-time to signal off-time ratio in the range of about 2:1 to about 1:2, preferably about 1:1, with signal on-times and off-times programmed in the range from about 10 seconds to about 5 minutes, preferably about 60 seconds each; a signal frequency of 30 Hz or less, preferably 15 Hz or less, and more preferably about 10 Hz; and a pulse width within the range of about 50 μs to about 500 μs, preferably from about 200 μs to about 300 μs.

For example, as illustrated in FIG. 1, a neurostimulation system for stimulation of the vagus nerve 100 of a patient generally comprises pulse generator 10, lead assembly 60, stimulating nerve electrode assembly 70, external programming computer 160 and programming wand 170. Pulse generator 10 is provided with a main body 30 comprising a case or shell 27 with a header 40 having one or more connectors 50 (shown in FIG. 2) for connecting to lead 60. The generator 10 is implanted in the patient's chest in a pocket or cavity formed by the implanting surgeon below the skin (indicated by broken line 90), similar to the implantation procedure for a pacemaker pulse generator. A stimulating nerve electrode assembly 70, preferably comprising an electrode pair 72,74 is conductively connected to the distal end of an insulated electrically conductive lead assembly 60, which preferably comprises a pair of lead wires (one wire for each electrode of an electrode pair). Each lead wire in lead assembly 60 is attached at its proximal end to a connector 50 on case 27. The electrode assembly 70 is surgically coupled to a vagus nerve 100 in the patient's neck.

Figure 3:
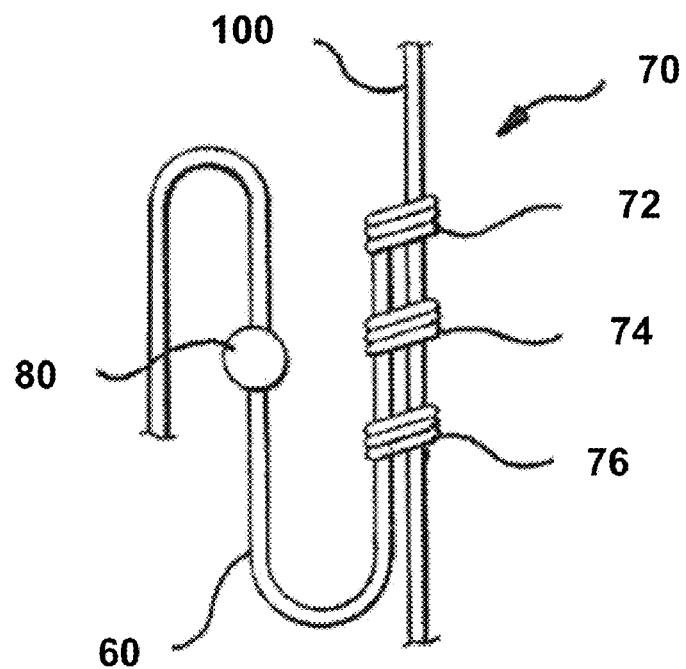
FIG. 3 is a simplified illustration of the lead and electrode configuration, as shown in FIG. 1, suitable for attaching to a vagus nerve of a patient, in accordance with an embodiment of the present invention.
Figure 4:
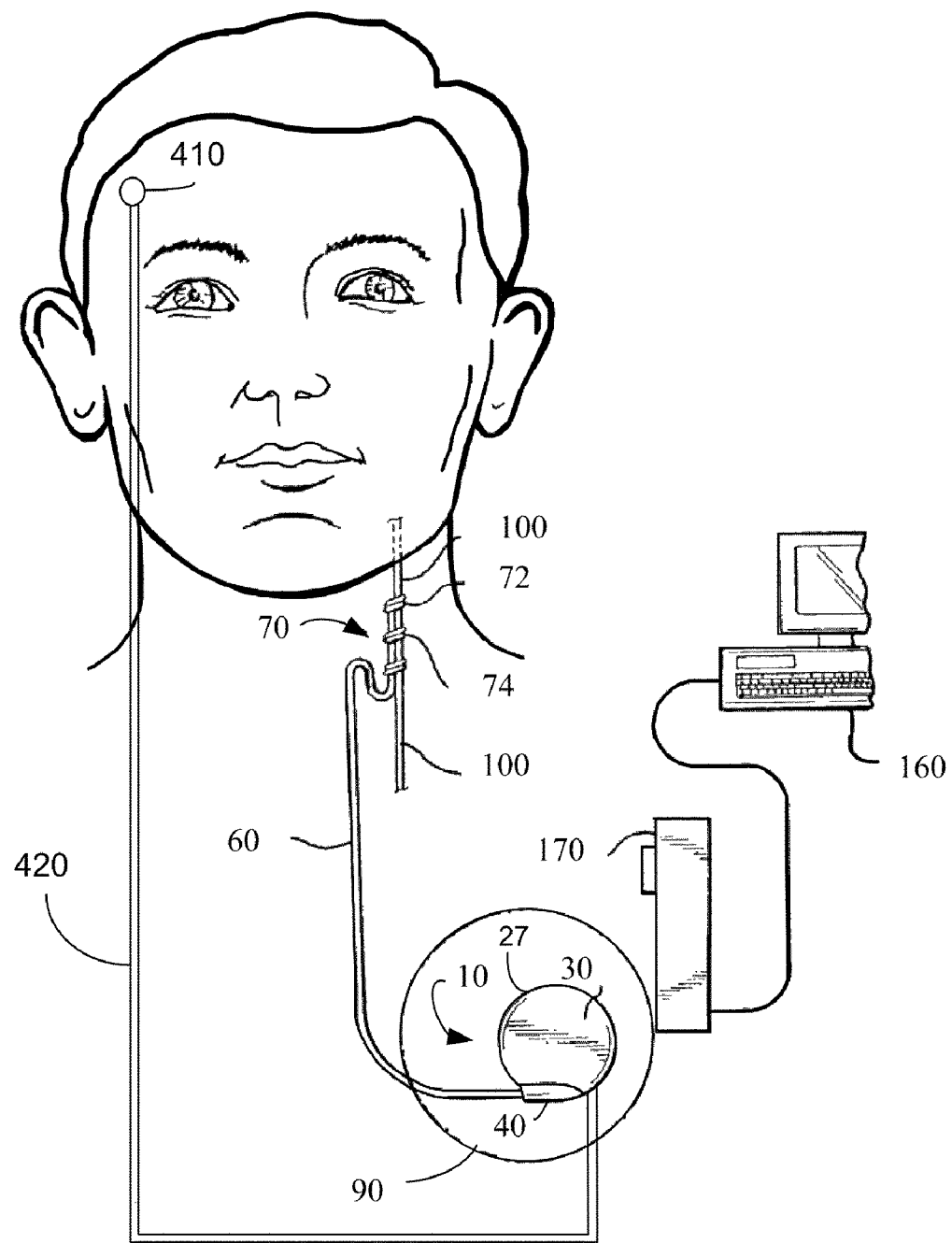
FIG. 4 is a simplified illustration of an implantable pulse generator (neurostimulator device) for stimulus generation with associated lead-electrode system implanted in a patient's body for stimulating a vagus nerve, showing a related external program console and an electroencephalographic sensor, in accordance with an embodiment of the present invention.
Figure 5:
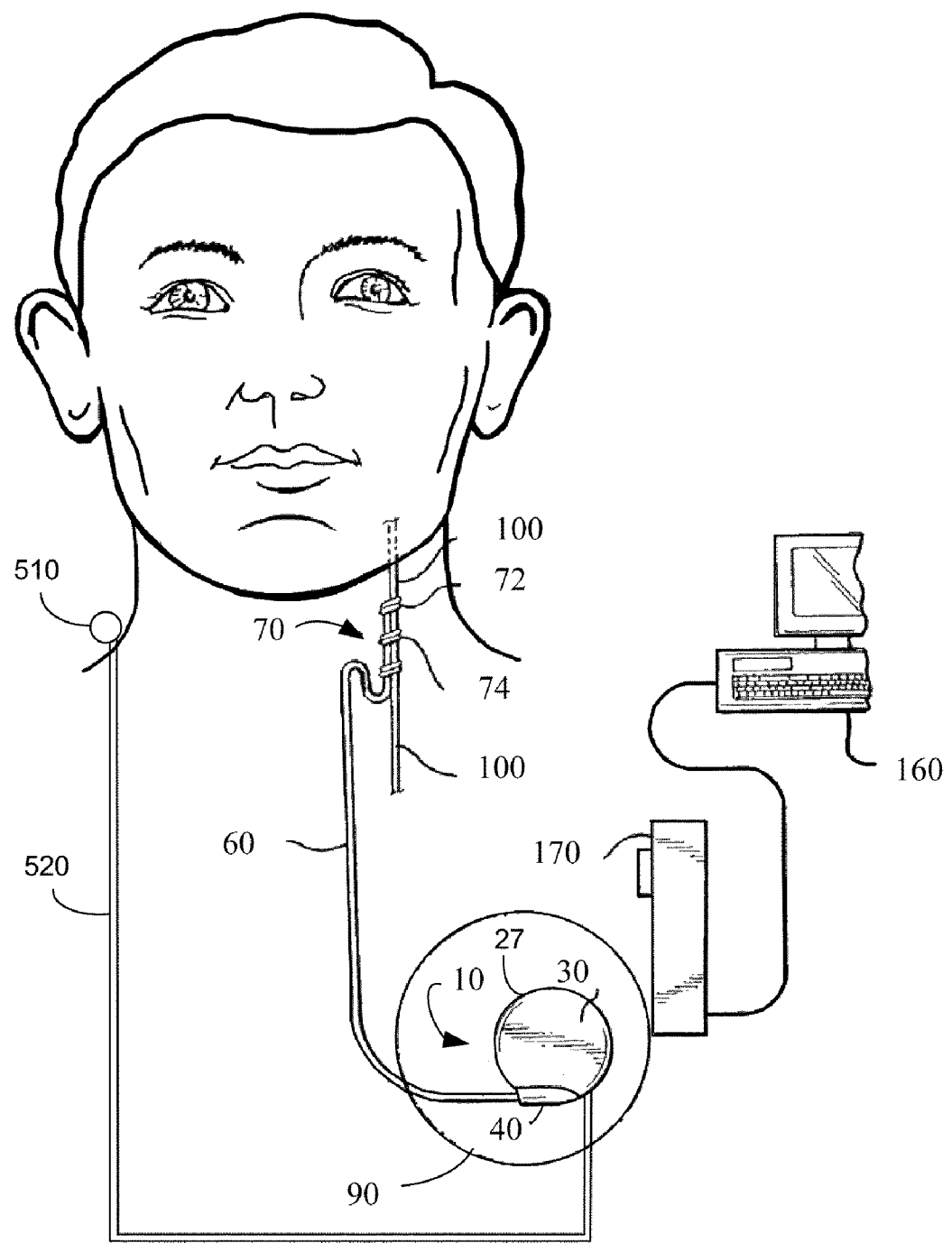
FIG. 5 is a simplified illustration of an implantable pulse generator (neurostimulator device) for stimulus generation with associated lead-electrode system implanted in a patient's body for stimulating a vagus nerve, showing a related external program console and a tremor sensor, in accordance with an embodiment of the present invention.
Figure 6:
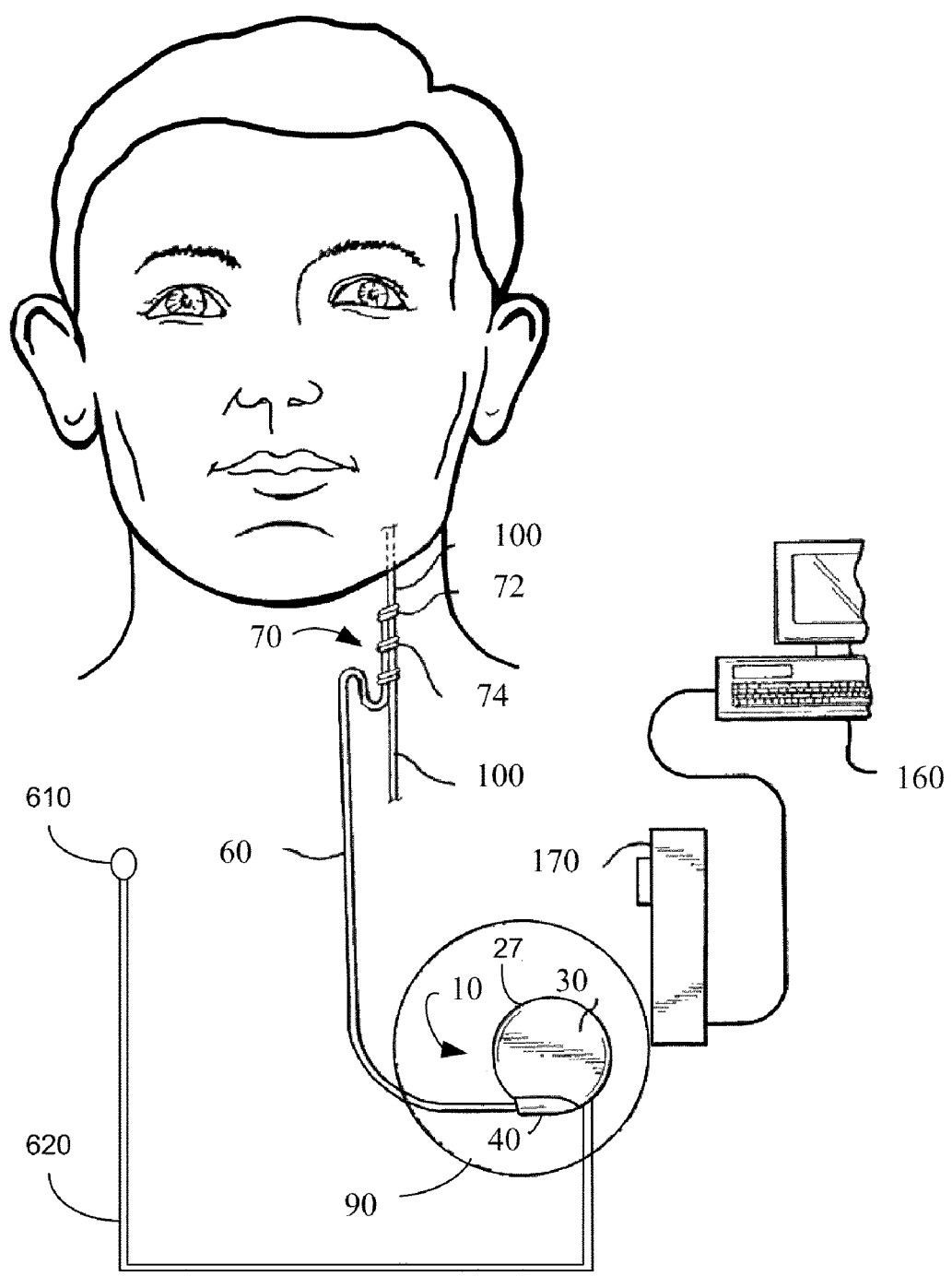
FIG. 6 is a simplified illustration of an implantable pulse generator (neurostimulator device) for stimulus generation with associated lead-electrode system implanted in a patient's body for stimulating a vagus nerve, showing a related external program console and a muscular sensor, in accordance with an embodiment of the present invention.

Referring now to FIG. 3, the electrode assembly 70 preferably comprises a bipolar stimulating electrode pair such as the electrode pair described in U.S. Pat. No. 4,573,481 (Bullara). The two electrodes are preferably wrapped about the vagus nerve, and the assembly 70 is preferably secured to the nerve 100 by a spiral anchoring tether 76 such as that described in U.S. Pat. No. 4,979,511 (Terry). Lead assembly 60 is secured, while retaining the ability to flex with movement of the chest and neck, by a suture connection 80 to nearby tissue. Although one of skill in the art will appreciate that many other electrode designs could be used in the present methods, a preferred electrode assembly 70 has an open helical design, as described in the above-referenced patent to Bullara, which is self-sizing and flexible, minimizes mechanical trauma to the nerve and allows body fluid interchange with the nerve. The electrode assembly 70 preferably conforms to the shape of the nerve, providing a low stimulation threshold by allowing a large stimulation contact area with the nerve. For instance, the electrode assembly 70 may comprise two electrode ribbons (not shown) of a conductive material such as platinum, iridium, a platinum-iridium alloy, and/or oxides of the foregoing metals. The electrode ribbons are preferably individually bonded to an inside surface of an elastomeric body portion of the two spiral electrodes 72,74, which may comprise two spiral loops of a three-loop helical assembly.

The lead assembly 60 may comprise two distinct lead wires or a coaxial cable whose two conductive elements are respectively coupled to one of the conductive electrode ribbons 72,74. One suitable way of coupling the lead wires or cable to the electrodes comprises a spacer assembly such as that disclosed in U.S. Pat. No. 5,532,778, although other know coupling techniques could be used also. The elastomeric body portion of each loop is preferably composed of silicone rubber, and the third loop 76, which typically has no electrode, acts as the anchoring tether for the electrode assembly 70.

Figure 2:
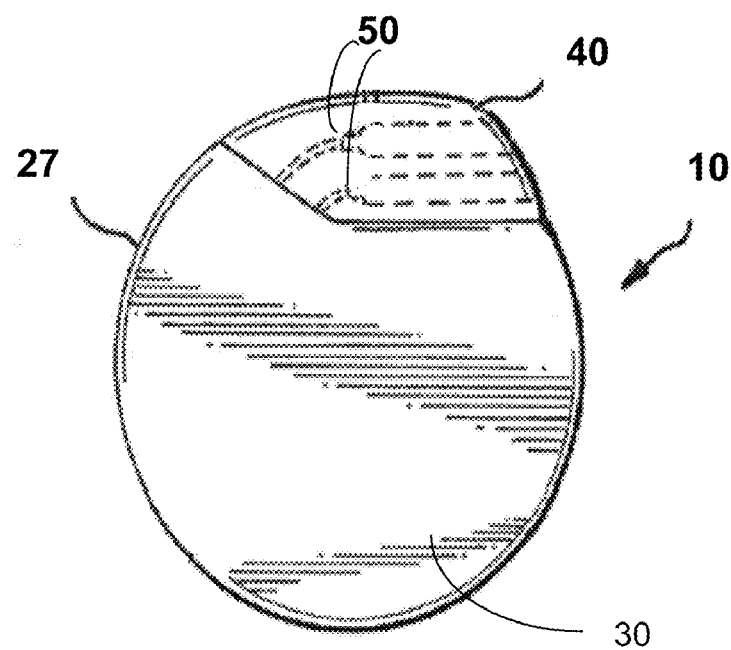
FIG. 2 is a front view of the implantable pulse generator of FIG. 1, showing the header and electrical connectors for coupling the device to a lead/electrode assembly, according to an embodiment of the present invention.

Referring to FIGS. 1-3, according to an exemplary embodiment the neurostimulator system for stimulating a patient's vagus nerve comprises an electrical pulse generator 10 provided with a shell or case 27 of a biocompatible material for protecting circuitry of the pulse generator from the body environment. The case preferably includes a header 40 made of a biocompatible material such as polyurethane, with multiple connectors 50 for connecting leads 60. The electrical pulse generator is preferably implanted in the patient's chest or axilla area.

A stimulating nerve electrode assembly 70 comprising an electrode pair is conductively connected to the distal end of an insulated electrically conductive lead assembly 60 that comprises a pair of lead wires (one wire for each electrode of an electrode pair). Each lead wire is attached at its proximal end to one of the connectors 50. As shown in FIG. 1, the electrode assembly is preferably coupled to the left vagus nerve in the patient's neck with the cathode located proximal to the brain and the anode located distal to the brain relative to the cathode.

The electrical pulse generator generates electrical signals as waveform pulses according to a variety of programmable parameters including the magnitude of the electric current, the pulse width, pulse frequency, as well as the on- and off-time of the stimulation and non-stimulation periods.

In a particular example, the programmable parameters of the electrical pulse generator used for the manufacture of a neurostimulator system were set as follows: the current was set to 1 mA, the stimulation on-time to 62 s, the stimulation off-time to 60 s, the signal frequency to 10 Hz and the pulse width to 250 μsec.

Compared to vagus nerve stimulation treatment for epilepsy, the above parameters represent low-frequency, high duty-cycle stimulation. The current intensity used produced no adverse effects.

The thus specified neurostimulator system was applied to a patient suffering from persistent CT who was scored 32/40 according to the so-called Klockgether-Rating-Scale (Klockgether T, Ludtke R, Kramer B, et al., The natural history of degenerative ataxia: a retrospective study in 466 patients, Brain, vol. 121, pp. 589-600, 1998). This scale is based on a five-point rating system evaluating dys-dyadochokinesia, intention tremor, dysartria, upper and lower limb ataxia, gait and stance. Mild disability scored 1 point, maximum disability 5 points.

Three months and six months later, the evaluated Klock-gether-Rating-Scale score was 28/40 and 24/40, respectively.

Whereas the exact mechanism of influencing and controlling CT associated with MS by electrical stimulation is yet not known, one may speculate that the applied periodic stimulation with relatively low-frequency at relatively high duty-cycles of almost time-equivalent on- and off-times may disrupt the pathologically modified rhythmicity of inferior olive that is commonly regarded as a crucial factor in cerebellar tremor.

Without further elaboration, it is believed that one skilled in the art can, using the description herein, utilize the above-described apparatus and methods to their fullest extents. The foregoing embodiments are to be construed as illustrative, and not as constraining the remainder of the disclosure in any way whatsoever. Many variations and modifications of the embodiments disclosed herein are possible and are within the scope of the invention as defined by the appended claims. Accordingly, the scope of protection is not limited by the description set out above, but is only limited by the claims which follow, that scope including all equivalents of the subject matter of the claims. The disclosures of all patents, patent applications and publications cited herein are hereby incorporated herein by reference, to the extent that they provide exemplary, procedural or other details supplementary to those set forth herein.

What is claimed is:

1. A neurostimulator system for alleviating cerebellar tremor, comprising:
    a programmable electrical pulse generator; and
    at least one electrode connected to the programmable electrical pulse generator and configured to apply electrical signals to a cranial nerve; and wherein
    the programmable electrical pulse generator is programmed to generate electrical signals with a combination of parameters that is effective in reducing cerebellar tremor, the combination of parameters comprising:
        a signal frequency of 15 Hz or less,
        a current magnitude of about 1 mA or less,
        a stimulation signal on-time to signal off-time ratio in the range of 2:1 to 1:1.8;
        signal on-times and off-times in the range of about 10 seconds to about 5 minutes, and
        a pulse width within the range of 50 µs to 300 µs.

2. The neurostimulator system according to claim 1, further comprising:
    an electroencephalographic sensor configured to detect a presence, onset, or precursors of cerebellar tremor associated with multiple sclerosis by sensing electroencephalographic waves and to output at least one first sensor signal to the electrical pulse generator, wherein the electrical pulse generator is configured to generate electrical signals on the basis of the at least one first sensor signal.

3. The neurostimulator system according to claim 1, further comprising:
    a tremor sensor connected with the programmable electrical pulse generator and configured to sense tremor associated with multiple sclerosis, to generate at least one second sensor signal, and to transmit the at least one second sensor signal to the programmable electrical pulse generator, wherein the electrical pulse generator is configured to generate electrical signals on the basis of the at least one second sensor signal.

4. The neurostimulator system according to claim 1, further comprising
    a muscular sensor connected with the programmable electrical pulse generator and configured to sense muscle activity, to generate at least one third sensor signal and to transmit the at least one third sensor signal to the programmable electrical pulse generator, wherein the electrical pulse generator is configured to generate electrical signals on the basis of the at least one third sensor signal.

5. The neurostimulator system according to claim 1, wherein the at least one electrode comprises a first electrode and a second electrode wherein the first electrode has a negative potential with respect to the second electrode.

6. The neurostimulator system of claim 1, wherein the programmable electrical pulse generator is programmed to generate signals with the following parameters:
    a signal frequency of about 10 Hz;
    a current magnitude of about 1 mA;
    a pulse width of about 250 µs;
    a signal on time of about 60 seconds; and
    a signal on-time to signal off-time ratio of about 1:1.

7. A method for manufacturing a neurostimulator system intended for alleviating cerebellar tremor associated with multiple sclerosis, comprising:
    providing a programmable electrical pulse generator;
    programming the programmable electrical pulse generator to generate electrical signals effective to control cerebellar tremor when said signals are applied to a cranial nerve of a patient suffering from cerebellar tremor; and
    providing at least one electrode connected with the programmable electrical pulse generator for applying the electrical signals generated by the electrical pulse generator to a cranial nerve for controlling cerebellar tremor,
    wherein the programmable electrical pulse generator is programmed to generate electrical signals having a current magnitude of about 1 mA or less, a stimulation signal on-time to signal off-time ratio in the range of 2:1 to 1:1.8, signal on-times and off-times in the range of about 10 seconds to about 5 minutes, a signal frequency below a frequency of 15 Hz, and a pulse width within the range of 50 µs to 300 µs.

8. The method according to claim 7, wherein the electrical signals are pulsed waveform signals.

9. The method according to claim 7, wherein programming the pulse generator comprises providing for the electrical signals to be delivered continuously or periodically or intermittently and/or on the patient's demand.

10. The method according to claim 7, wherein the programmable electrical pulse generator is programmed by programmable parameters comprising a pulse width and/or a current magnitude and/or a pulse frequency and/or stimulation on-time and/or stimulation off-time.

11. The method according to claim 7, wherein the at least one electrode comprises a first electrode and a second electrode, wherein the first electrode has a negative potential with respect to the second electrode.

12. The method according to claim 7, further comprising providing a sensor configured to sense a presence, onset, or precursors of cerebellar tremor by sensing electroencephalographic waves and to output at least one first sensor signal to the electrical pulse generator, wherein the electrical pulse generator is configured to generate electrical signals on the basis of the at least one first sensor signal.

13. The method according to claim 7, further comprising providing a muscular sensor configured to sense a presence, onset, or precursors of cerebellar tremor by sensing spontaneous muscle activity and to output at least one muscle sensor signal to the electrical pulse generator, wherein the electrical pulse generator is configured to generate electrical signals on the basis of the at least one muscle sensor signal.

14. The method according to claim 7, wherein the operation of programming the programmable electrical pulse generator to generate electrical signals effective to control cerebellar tremor comprises programming the programmable electrical pulse generator to generate electrical signals with attributes comprising:
current magnitude of about 1 mA;
signal frequency of about 10 Hz;
pulse width of about 250 µs;
signal on time of about 60 seconds; and
signal on-time to signal off-time ratio of about 1:1.

15. A method of treating a patient suffering from cerebellar tremor, comprising:
providing a neurostimulator system comprising a programmable electrical pulse generator comprising at least one electrode for applying electrical signals generated by the electrical pulse generator, wherein said pulse generator is programmed with signal parameters comprising a pulse width, a current magnitude, a pulse frequency, stimulation on-time and stimulation off-time effective to attenuate or control cerebellar tremor in the patient;
placing said electrode in electrical communication with a cranial nerve of the patient; and
applying said electrical signals to said cranial nerve by means of the at least one electrode, said application of said electrical signals being effective to attenuate or control the cerebellar tremor:
wherein the following programmable parameters are used:
current magnitude of about 1 mA or less;
pulse width within the range of 50 µs to 300 µs;
signal frequency below 15 Hz;
signal on-times and off-times in the range of about 10 seconds to about 5 minutes; and
a stimulation signal on-time to signal off-time ratio in the range of 2:1 to 1:1.8.

16. The method according to claim 15, wherein the cerebellar tremor is associated with multiple sclerosis.

17. The method according to claim 15, wherein the electrical signals are pulsed waveform signals.

18. The method according to claim 15, wherein the electrical signals are applied continuously or periodically or intermittently and/or on the patient's demand.

19. The method according to claim 15, wherein said at least one electrode comprises first and second electrodes and the electrical signals are applied by said first electrode and said second electrode wherein the first electrode has a negative potential with respect to the second electrode and wherein the first electrode is applied proximal to the patient's brain and the second electrode is applied distal to the patient's brain with respect to the first electrode.

20. The method according to claim 15, wherein the neurostimulator system comprises a sensor configured to sense an onset or precursors of cerebellar tremor and wherein the electrical pulse generator is configured to generate electrical signals on the basis of at least one first sensor signal,
said method further comprising sensing electroencephalographic waves and outputting at least one first sensor signal to the electrical pulse generator.

21. The method according to claim 15, wherein the neurostimulator system comprises a muscular sensor configured to sense an onset or precursors of cerebellar tremor by sensing muscle activity and to output at least one muscular sensor signal to the electrical pulse generator, and wherein the electrical pulse generator is configured to generate electrical signals on the basis of the at least one muscular sensor signal.

22. The method according to claim 15, wherein:
the current magnitude is set to about 1 mA;
signal frequency is set to about 10 Hz;
pulse width is set to about 250 µs;
signal on time is set to about 60 seconds; and
signal on-time to signal off-time ratio is set to about 1:1.

23. A non-transitory computer program product, comprising:
one or more non-transitory computer readable media having computer-executable instructions for controlling a programmable electrical pulse generator to generate electrical signals to be applied to a cranial nerve, the computer-executable instructions configured to cause the electrical signals to have attributes comprising:
a current magnitude about 1 mA or less,
a stimulation signal on-time to signal off-time ratio in the range of 2:1 to 1:1.8,
signal on-times and off-times in the range of about 10 seconds to about 5 minutes,
a signal frequency below 15 Hz, and
a pulse width within the range of 50 µs to 300 µs.

24. A non-transitory computer program product according to claim 23, wherein the computer-executable instructions are configured to cause the electrical signals to have attributes comprising:
current magnitude of about 1 mA;
signal frequency of about 10 Hz;
pulse width of about 250 µs;
signal on time of about 60 seconds; and
signal on-time to signal off-time ratio of about 1:1.

* * * * *